(12) United States Patent
O'Kelly

(10) Patent No.: US 6,856,837 B2
(45) Date of Patent: Feb. 15, 2005

(54) METHOD AND DEVICE FOR ELECTROCHEMICALLY BUILDING OF MUSCLE

(76) Inventor: Gregory C. O'Kelly, 392 Pismo St., San Luis Obispo, CA (US) 93401

( * ) Notice: Subject to any disclaimer, the term of this patent is extended or adjusted under 35 U.S.C. 154(b) by 54 days.

(21) Appl. No.: 10/301,048

(22) Filed: Nov. 20, 2002

(65) Prior Publication Data

US 2004/0098064 A1 May 20, 2004

(51) Int. Cl.[7] .................................................. A61N 1/32
(52) U.S. Cl. .......................................................... 607/50
(58) Field of Search .......................... 607/1, 2, 48, 49, 607/50–52, 72

(56) References Cited

U.S. PATENT DOCUMENTS

| | | | |
|---|---|---|---|
| 4,326,534 A | | 4/1982 | Axelgaard et al. |
| 4,342,317 A | | 8/1982 | Axelgaard |
| 4,408,609 A | | 10/1983 | Axelgaard |
| 4,580,570 A | * | 4/1986 | Sarrell et al. ................. 607/72 |
| 4,595,010 A | | 6/1986 | Radke |
| 4,712,558 A | | 12/1987 | Kidd et al. |
| 4,811,742 A | | 3/1989 | Hassel et al. |
| 4,832,033 A | | 5/1989 | Maher et al. |
| 4,838,272 A | | 6/1989 | Lieber |
| 5,097,833 A | | 3/1992 | Campos |
| 5,433,737 A | | 7/1995 | Aimone |
| 5,507,788 A | | 4/1996 | Lieber |
| 5,678,535 A | | 10/1997 | DiMarco |
| 5,871,534 A | | 2/1999 | Messick et al. |
| 5,911,218 A | | 6/1999 | DiMarco |
| 5,974,342 A | * | 10/1999 | Petrofsky ..................... 607/50 |
| 6,330,476 B1 | | 12/2001 | Ben-Haim et al. |
| 6,363,279 B1 | | 3/2002 | Ben-Haim et al. |

OTHER PUBLICATIONS

Fairchild Semiconductor, CD4538BC Dual Precision Monostable, Oct. 1987, Revised Apr. 2002, pages.

* cited by examiner

Primary Examiner—George R. Evanisko
(74) Attorney, Agent, or Firm—Coudert Brothers LLP

(57) ABSTRACT

A method and device are disclosed for using electrochemistry to build and strengthen muscles by applying pulses of DC electrical charge, at a duration in the range of about 0.2 to about 1 millisecond and a frequency of at least 1000 Hertz, to the skin by means of an anodic probe overlying the motor endplate regions/neuromuscular junctions of the muscle at such a strength to cause the muscle to twitch or only slightly contract with each pulse. The DC is applied at current amplitude of from about 5 to about 25 milliamperes, and a voltage in the range of about 50 to about 120 volts. A DC power source is used to deliver the electrical charge, preferably of at least 3 watts.

14 Claims, 3 Drawing Sheets

METHOD AND DEVICE FOR ELECTROCHEMICALLY BUILDING OF MUSCLE

FIELD OF INVENTION

The present invention relates to a method and device for strengthening and building muscle. More particularly, the invention relates to using electrical impulses for building muscle through the use of electrochemistry.

BACKGROUND OF THE INVENTION

The use of electricity to build or strengthen muscle has a long history of questionable claims. These claims are unsubstantiated for the most part. Neither NASA nor any professional athlete or body builder uses the technique, relying instead on traditional resistance exercises.

Rehabilitationists, chiropractors, and doctors of physical medicine still subject patients to the rigors of electrotherapy. They claim that it has some effect on the alteration of muscle structure yet are unable to given any specifics about such changes in structure. Endorsements of electrotherapy in building muscle are based upon changes in performance of the patient. These changes are so inconsiderable that electrotherapy has yet to escape a clinical setting or demonstrate more effectiveness than the placebo effect.

The clinical inconsequence of electrotherapy is due to the following three things:

(1) The traditional reliance upon the electrotherapeutic use of alternating or faradic current. Such current is incapable of inducing chemical changes of any sort, and is used mainly for either voltage transmission or the transduction of mechanical energy. If electricity is thought of as a fluid, then alternating current passes on fluid pressure while direct current passes on that pressure and the fluid itself.

(2) The desire to avoid ionization of the skin, when direct or galvanic current is used, prevents the electrotherapist from appreciating the electronic nature of electricity and the role of electrons in all chemical binding, especially that of organic chemistry. Direct current or chemical energy is electrons, as cathode rays or beta radiation, that results in ionization of the skin, something that does not result from the use of alternating or faradic current.

(3) Finally, electrotherapists triggering muscle contractions using electricity are not aware that to build muscle in this manner the impulse must be analogous to that which the body uses. The body does not use alternating current. It uses direct current (DC) in the form of electrochemistry. In addition, the impulse is delivered by the nerve to the site of the neuromuscular junction or motor endplate region, and not to the surface of muscle groups in a haphazard manner.

During WWII four researchers for the Veterans Administration of the time [Guttman, Melville, Wehrmacher, Hines] found that those receiving what was called 'galvanic exercise' for hands atrophic from disuse following an ulnar nerve lesion later repaired by surgery, recovered muscle bulk and strength of use far faster than those restricted to physical therapy only. The results of the clinical testing were noted and never expanded upon. Electrotherapists retained the use of faradic or alternating current (AC) because AC did not require the expensive switching equipment to turn the current on and off repeatedly for each new muscle twitch. Nor does AC cause skin problems if allowed to run on for more than 10 seconds. A paper on the treatment of bioelectricity appeared the following decade and spoke of bioelectricity in terms of the movement of ions, as if electricity were atomic or molecular rather than electronic. This account, awarded Nobel prizes in 1963 and 1978, is the standard explanation for nervous system and cellular functioning even today. This account does not distinguish between AC and DC, nor does it treat bioelectricity as involving electron movement at all. It is incapable of exploiting the health benefits of electrochemistry or of discerning why electrotherapy using alternating current has no consequence. Consequently the electrotherapy still practiced resorts exclusively to the use of alternating or faradic current.

There is a need for a more effective system for exploiting the health benefits of electrochemistry through the use of DC.

SUMMARY OF THE INVENTION

The present invention is directed to building and strengthening muscles by delivering pulses of electrical charge transcutaneously by means of an anode of DC to the site of the neuromuscular junction or motor endplate region.

The method of present invention uses electrochemistry to build and strengthen muscles by applying pulses of DC electrical charge, at a duration in the range of about 0.2 to about 1 millisecond (referred to herein as the pulse width) and a frequency of at least 1000 hertz (referred to herein as the pulse rate), to the skin by means of an anodic probe overlying the motor endplate regions/neuromuscular junctions of the muscle at such a strength to cause the muscle to only slightly contract. The DC is applied at a current amplitude of from about 5 to about 25 milliamperes, and a voltage in the range of about 50 to about 100 volts. A DC power source is used to deliver the electrical charge, preferably of at least 3 watts.

One embodiment of a device for carrying out the method of the present invention includes the following elements:

a power supply that produces a power signal at a power output terminal, the power signal having a current amplitude range from about 5 to about 25 milliamperes, and a DC voltage range from about 50 to about 120 volts;

a pulse generator that operates to generate a pulse signal that has a pulse duration in the range of about 0.2 to about 1 millisecond, and a pulse frequency in the range of about 1000 to about 2500 Hertz;

a switching circuit that is coupled to receive the pulse signal, the switching circuit has a switching output terminal, and in response to the pulse signal, the switching circuit operates to couple and uncouple the switching output terminal to a system ground;

a cathode having a first end that is detachably attached to the switching output terminal and a second end that is positioned on the body of a user; and an anodic probe having a first end that is detachably attached to the power output terminal, and a second end that comprises a probe.

The muscle is built and strengthened using this system by selectively touching the probe to a site on the skin overlying the motor endplate regions/neuromuscular junctions of the muscle for a duration in the range of about 1 second to about 8 seconds per treatment at least two times a week. The level of current amplitude delivered to the user depends upon the depth of the motor endplate region beneath the skin.

BRIEF DESCRIPTION OF THE DRAWINGS

Further features and advantages will become apparent from the following and more particular description of the preferred embodiments of the invention, as illustrated in the accompanying drawings in which.

DETAILED DESCRIPTION OF THE INVENTION

Figure 1:
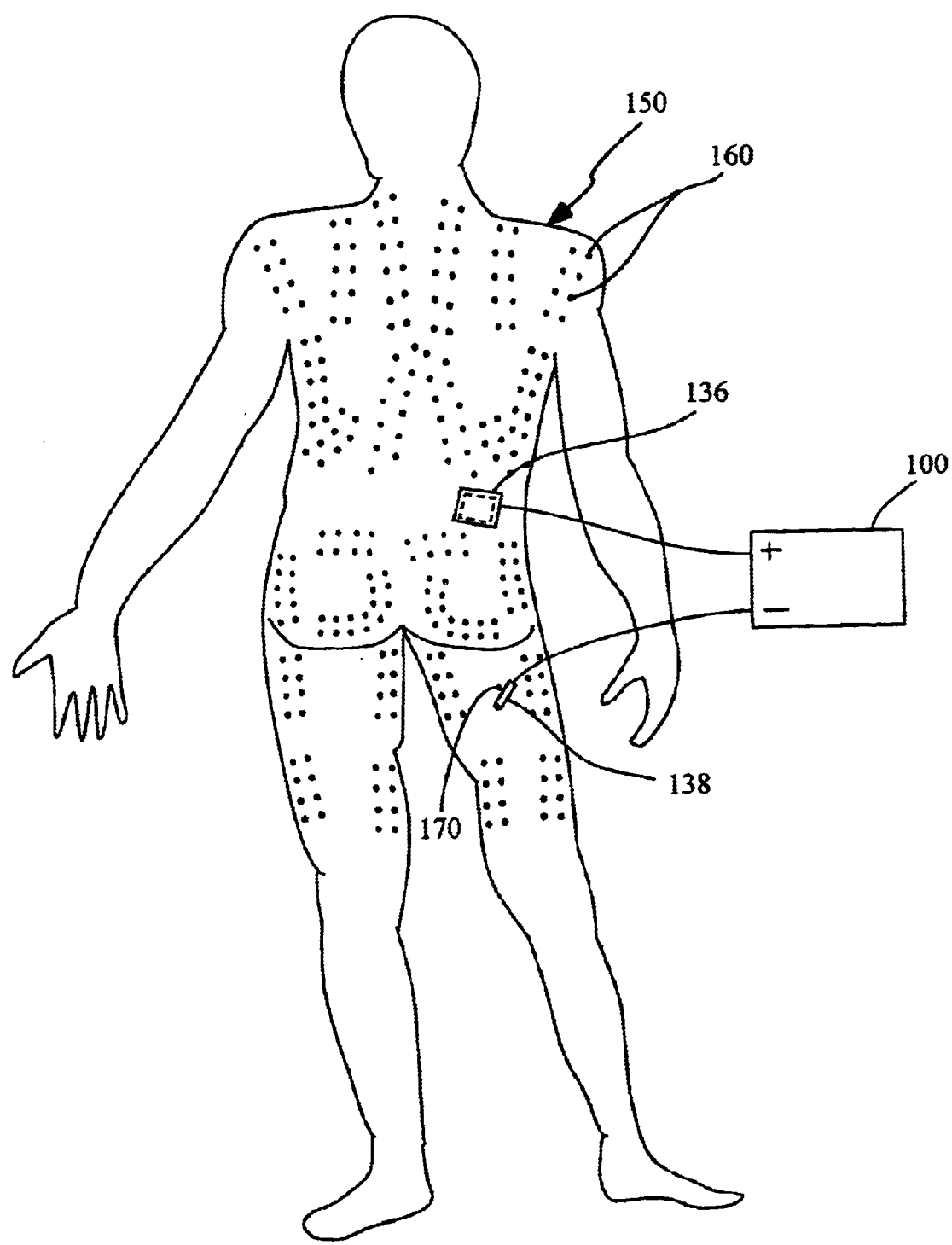
FIG. 1 is a block diagram of the present invention.
Figure 2:
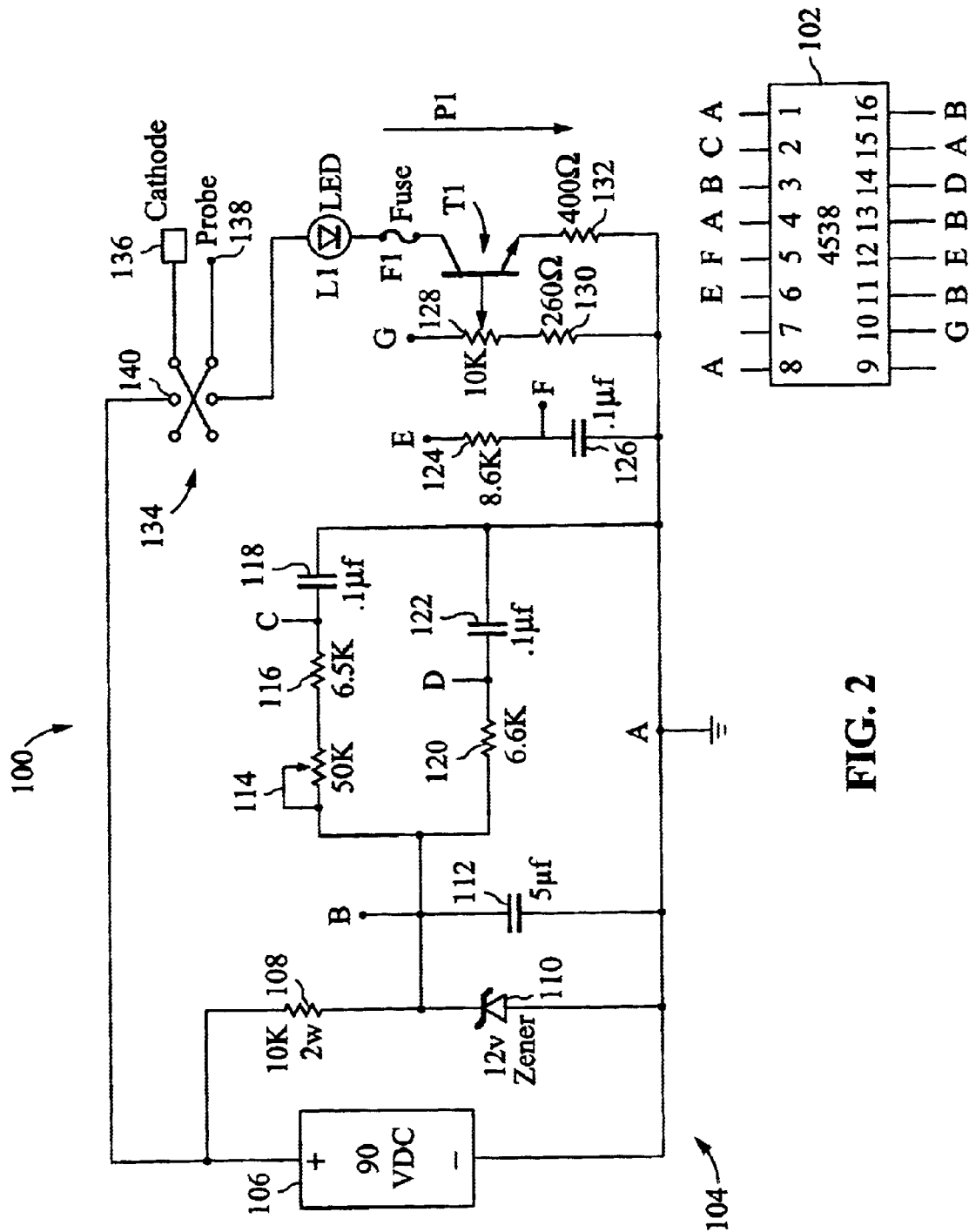
FIG. 2 is a block schematic diagram of one embodiment of the present invention.
Figure 3:
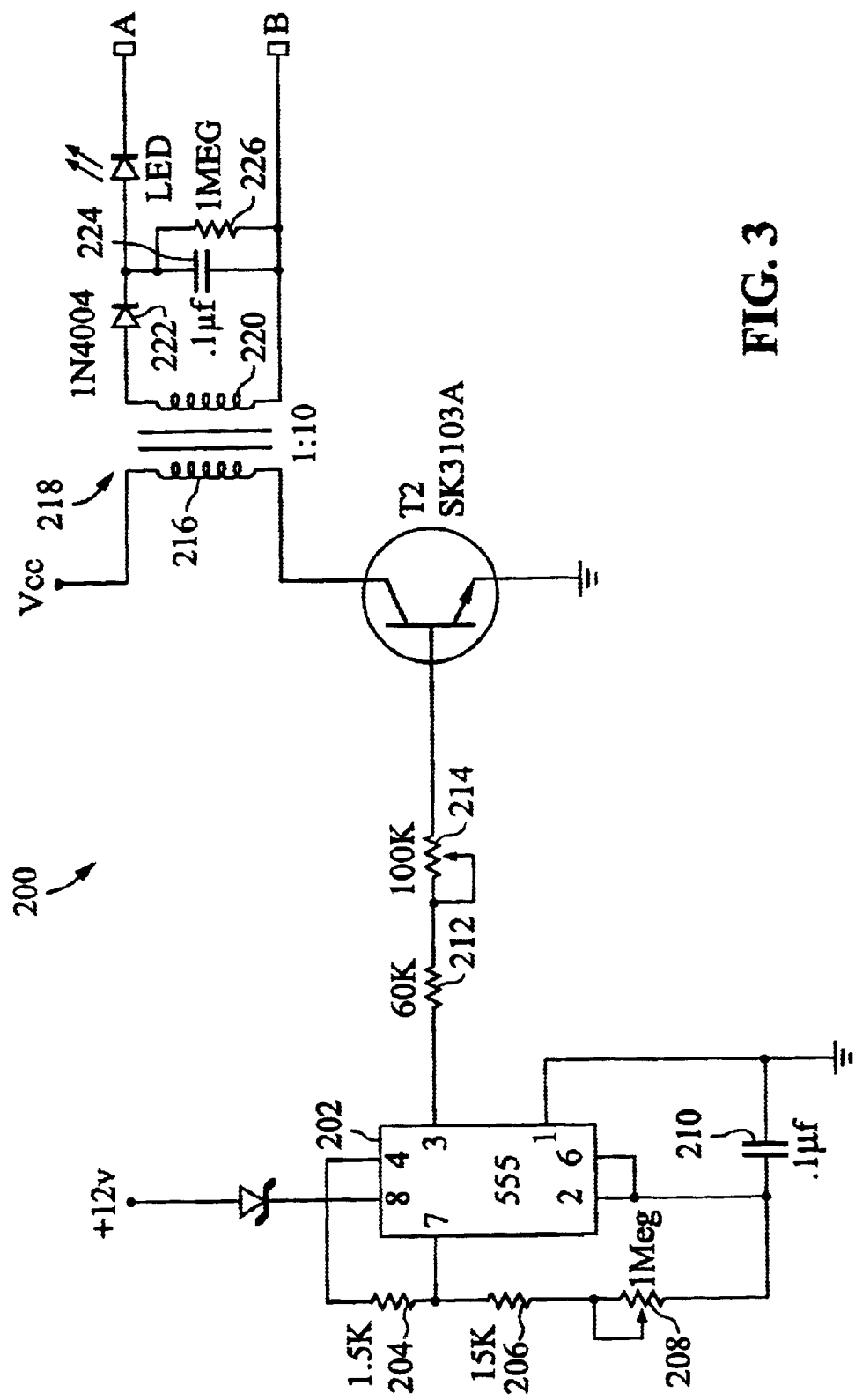
FIG. 3 is a block schematic diagram of an alternate embodiment of the present invention.

FIGS. 1–2 show device 100 for generating pulses to stimulate a muscle's transverse tubule in accordance with the present invention. The device 100 includes a switching circuit 102 and associated circuitry that is generally shown at 104. The switching circuit is preferably a CMOS 4538 solid-state integrated circuit. However, other switching circuits are suitable for use in other embodiments of the invention.

Device 100 includes a 90-volt DC power source 106 that has a positive output coupled to a power resistor 108 and a 12-volt zener diode 110. In a preferred embodiment, AC from a wall socket is transformed and rectified by a transformer/rectifier (not shown) to achieve the required DC voltage. A negative output of the power source 106 is coupled to a system ground at Node A of circuit 102. The power source 106 is used to generate a 12-volt DC signal at node B, which is coupled to a system ground through capacitor 112. Node B is also coupled to two timing circuits. The first timing circuit comprises potentiometer 114, resistor 116 and capacitor 118. A terminal (Node C) is defined at the coupling between the resistor 116 and the capacitor 118. The second timing circuit comprises resistor 120, capacitor 122, and a Node D terminal defined at the coupling between resistor 120 and capacitor 122. Capacitors 118 and 122 are also coupled to the system ground.

A Node E terminal is coupled to resistor 124, which in turn is coupled to capacitor 126 at Node F. Capacitor 126 is also coupled to the system ground. A Node G terminal is coupled to potentiometer 128 that is also coupled to resistor 130. The center wipe of the potentiometer 128 is connected to a base terminal of transistor T1. An emitter terminal of T1 is connected to resistor 132, and a collector terminal of T1 is connected to fuse F1, which is preferable a 0.3 amp fast blow fuse. Preferably transistor T1 is a Philips EGC 396 transistor or equivalent.

An LED (L1) is connected between the fuse F1 and a cross-connect 134. The cross-connect is coupled to a cathode terminal 136 and a probe terminal 138. The cathode 136 preferable comprises a corrodible metal, e.g., iron. The cross-connect is used to selectively connect the cathode and probe terminals to the circuit. The switching circuit 102 is an integrated circuit that is connected to the circuitry 140 according to the terminals indicated at each pin of the circuit 102. For example, pins 1, 4, 8, and 15 of the switching circuit are all connected to terminal Node A. Thus, the switching circuit 102 and the circuitry 104 operate together to generate pulses in accordance with the present invention.

During operation, 90 volts DC from the power source 106 appears at terminal 140 of the cross connect 134. Assuming the corroding cathode 136 and probe 138 are connected into circuit, operation of the switching circuit 102 causes pulses to appear at Node G, which selectively activates transistor T1. When T1 is "turned on," current can flow through path P1 when cathode 136 is positioned at any suitable position on the skin of a user 150 and probe terminal 138 is touched to the skin of user 150. An LED is provided to indicate when current is flowing through P1.

By adjusting the timing circuits, it is possible to achieve various pulse rates and current amplitudes as discussed in detail below. Particularly, this may be accomplished by adjusting potentiometers 114 and 128. Therefore, when cathode 136 and probe 138 are connected into the circuit by means of the cross-connect 134, and attached to the skin of user 150, pulses generated by the switch control circuit 102 control current flowing down path P1, and thereby energize the muscle cell's transverse tubule in accordance with the present invention. Touching the head of probe 138 to any one of the sites 160 on the skin of user 150 at, for example, a pulse rate of 2000 Hz., with a pulse width of 0.25 milliseconds, and a current strength variable between 5 and 20 milliamperes, depending upon the depth of the motor endplate region and 85 to 90 volts, is sufficient to overload any and all muscles of the body in just one second of treatment time for each and every motor endplate region or ganglion. Preferably probe 138 is wand-like and has a switch 170 for turning the switching circuit 102 on and off. The head of probe 138 is stationary. However, it is contemplated that probe 138 can have a swivel head or a roller head.

FIG. 2 shows an alternate embodiment comprising device 200 for generating pulses to stimulate a muscle cell's transverse tubule in accordance with the present invention. The device 200 includes a switching circuit 202 that is preferably a 555 timer circuit. Timer circuit 202 is connected to timing components that comprise resistors 204 and 206, potentiometer 208, and capacitor 210. An output signal of timing circuit 202 is provided at pin 3 and comprises a sequence of pulses that are coupled to a base terminal transistor T2 through resistor 212 and potentiometer 214. Transistor T2 is preferably of type SK3103A and has its emitter terminal connected to a system ground. Other similar transistor types may also be substituted for transistor T2.

A collector terminal of transistor T2 is connected to one leg 216 of a flyback transformer 218. The transformer 218 steps up its input voltage by ten times. Thus, at output leg 220, the voltage is ten times the voltage at input leg 216. Components diode 222, capacitor 224, and resistor 226 provide some rectification and filtering of the output. An LED is also provided to indicate when current is flowing to output probes connected to terminals A and B. Terminals A and B may be connected to cathode 136 and probe 138 as described in previous embodiments.

In accordance with this embodiment, the timer circuit 202 operates to output pulses that turn transistor T2 on and off. When T2 is in the on state, 12 volts, that can be generated by an automobile battery, is placed across the input leg 216 of the transformer 218. This causes ten times that voltage to appear across the output leg 220 of the transformer. This high voltage pulsed signal is provided at the output terminals A and B for connection to the skin of user 150 in accordance with the present invention. The pulse duration and amplitude may be adjusted using potentiometers 208 and 214 to achieve selected levels.

By using the alternate embodiment described above, current flow will be one tenth what it was at the input. Transformers only work with ever-changing voltages so that as the pulse width of a square wave is increased the transformer looses its effectiveness since it works only so long as voltage is changing, not remaining the same during a pulse. This means that wider pulse widths do not result in increased current. But shorter pulse widths like those needed to achieve 2000 pulses per second do not allow enough time for the current, with its time factor as a rate of flow of electrons, to be very great either. Although equipment using flyback transformers rather than capacitors may provide the pulsed direct current needed to build muscle, they cannot be used effectively at pulse rates higher than 1000 Hz. because of the limits on the current. This extends treatment times not only for the individual site 160 on user 150 but also, since there are 1,152 of these sites, for a full body exercise session.

The pulses applied to one of these sites 160 on the skin by means of probe 138 are an exact simulation of the nature of the same nerve impulse, which causes the muscle to twitch or to slightly contract with each pulse from the probe These nerve impulses depend upon polarization, depolarization, and repolarization to function. Polarization and depolarization are triggered by the ionizing radiation of electrons. Therefore, by altering the pulse rate and pulse width by means of either switching circuit 102 or 202, each of the muscles under treatment can be overloaded just as if it were being used in weight training. In this way, the muscle can be built and strengthened without actually having to be used. Muscles too weak to be of use may be fortified, and user 150 does not have to be subjected to painful, exhausting, and mostly ineffectual sessions of physical therapy requiring the fortitude of the young and the healthy.

Beyond muscle building by the measured and precise delivery of beta radiation to the body, consideration of the distribution of nerve endings and their universal method of functioning suggests the possible restoration of all post-synaptic structures. All nerve fibers emerging from the brain and spinal cord and terminating in a peripheral, chemical synapse function by the transmission of chemical energy. This is called nervous system trophism. This trophism acts on all post-synaptic structures, be they muscles or organs or glands. All chemical synapses occur in clusters, whether these clusters are called neuromuscular junctions, motor endplate regions, or ganglia. By delivering pulsed DC from probe terminal 138 to one of these sites, user 150 may energize the protein synthesis necessary for the growth and maintenance of all post-synaptic structures. This could provide a powerful antidote to the chronic and degenerative diseases of aging, which are mostly a result of trophoneurosis, the diminution or cessation of nerve impulses from the nervous tissue to post-synaptic structures.

All multicellular organisms with nervous systems embody two forms of chemical energy capture and production that contrasts with the battery-like generation of energy within the single cell that is the result of mitochondrial action. The cells of multicellular organisms with nervous systems can be seen as electrolytic cells rather than primary cells or batteries. Electrolytic cells are cells to which energy is introduced from an outside source. This is especially the case for the neurons that make up the nervous substance of these multicellular organisms; these nervous systems evolved so that the organisms could more effectively capture the energy needed for the organisms to survive and multiply. These two forms of energy capture occur as respiration and gastrulation. Respiration allows for the oxidation of carbon and the exhalation of carbon dioxide, and gastrulation allows for the breakdown of organic molecules through the corrosive action of digestive enzymes and acids. Both these processes liberate chemical energy in the form of electrons, and this energy is distributed throughout the body in what is known as nervous system trophism. In electrochemical terms these two processes or forms of energy capture are termed oxidation-reduction reactions. Contrasting with this method of energy capture is that of photosynthesis, which characterizes most if not all of plant life.

An oxidation-reduction reaction involves the movement of electrons from an exothermic, oxidative, catabolic chemical reaction to an endothermic, anabolic, reduction reaction like that necessary for the building of tissue. Similar oxidation-reduction reactions take place in a battery when there is current flow, with corrosive chemical reactions taking place at the cathode liberating electrons, which exit the battery at the anode, the ground of the battery. What is required for this oxidation-reduction dynamic, this movement of electrons, is: (1) the existence of a barrier across which a voltage may be measured between the two reactions, and (2) a load or resistance to the movement of the electrons. According to Ohm's law, $V=IR$, in which I is the rate of electron movement, R is the resistance to that movement, and V is the electrical pressure needed to drive those electrons against that resistance. In the case of multicellular organisms with nervous systems, the barrier is the cell membrane, with the catabolic reaction taking place in the stomach or lungs. A voltage may be measured from the stomach or lungs across the cell membrane of any cell in the organism's body. When such measurements are made, the ground electrode is internal to the cell while the cathodic electrode is in the stomach or lungs. The classical case of an electrolytic cell is that of a battery delivering current to a beaker or glass tube in which there are either ions of gas or in solution. The current, I, comes from the catabolic reaction in the battery external to the cell, but delivered to the electrolytic cell via the battery's anode. This arrangement is paralleled by the organism's catabolic digestion taking place in the gut, a space lying external to all the cells of the organism yet itself enclosed by the barrier of the membranes of those cells. This catabolic digestion provides chemical energy to the organism's cells. R or the load on the battery is the movement of ions within the electrolytic cell, whether that cell is a biological electrolytic cell or not. In the case of multicellular organisms with nervous systems the movement of those ions, usually calcium, potassium or sodium, provides delivery of the necessary catalysts for cellular chemical reactions needed for growth, division, protein synthesis, the splitting of ATP (Adenosine Triphosphate), and so on. ATP is the universal cellular, chemical energy storage and retrieval mechanism. The splitting of ATP to release energy is done by mitochondria in the cell, and the process is called mitochondrial respiration. The endothermic, anabolic, biochemical reactions catalyzed by the movement of ions are balanced by the exothermic, catabolic reactions involved in digestion and respiration of the organism.

Both upper and lower motor neurons that trigger muscle contractions do so by the movement of electrons to the peripheral, chemical synapses that are found in all of the 1,152 clusters of synapses in the motor endplate regions and ganglia distributed throughout the body. Not all of the synapses in each of these clusters can be traced back to a motor neuron, but all can be traced back to the nervous tissue, and all have the same purpose, that is, the delivery of nervous system trophism in the form of chemical energy (electrons) to whatever structures lie post-synaptically, whether these structures be muscle cells or organs.

To simulate a nerve impulse like that which causes a muscle to twitch, all that is required is the delivery of chemical energy by the anode of the direct current (galvanic current or monophasic current) to the site of the motor endplate region or ganglia. These sites are clusters of synapses. When this happens the simulation, like the actual nerve impulse necessary for muscle contraction, draws calcium ions to the post-synaptic muscle cell, and these ions not only break the vesicles of acetylcholine delivered by the axon to the synapse, but in so doing catalyze the mitochondrial splitting of ATP at the site. The energy released by this splitting then travels out to the type I muscle fiber as an 'action potential' moving along the muscle cell's transverse tubule. The transverse tubule or type II muscle fiber is a protein structure of varying cross-sectional area within the muscle cell. It makes up the bulk of the muscle and originates in the muscle cell's cytoplasm, extensively arborizing as a conductor of the action potential to all type I muscle fibers. Type I fibers are the fibers which actually do the mechanical contracting.

With the arrival of the action potential at the electrical synapses formed by the extensively arborizing transverse tubule, calcium ions are again drawn across the muscle cell's sarcolemma, or membrane, to catalyze the splitting of ATP at the muscle cell's sarcomere by the actin/myosin proteins found there. It is this secondary splitting of ATP, which energizes the twitch of those proteins that form the type I muscle fiber. The sum of these twitches is a muscle contraction.

What is involved in striated or voluntary muscle function is inherently an electrochemical process, one that cannot be simulated by anything but the anode of the direct current delivering a pulse to the site of the motor endplate region or ganglia. Not only is such simulation not possible using faradic, alternating, or symmetrically biphasic current, or any form of electricity not capable of electrochemistry, but also the DC pulse must be delivered to a specific site 160. The DC pulse must be delivered to one of the 1,152 motor endplate regions and ganglia found in the body.

Distribution of these sites is predictable and systematic, and they may be precisely located using probe terminal 138, which is able to drive electrons into the body to the depth needed to act upon the site as a simulation. There are 64 of these sites on either side of the head and neck, and, similarly, 64 sites on either side of the buttocks and down the back and outside of the thigh. In addition there are 128 sites on each limb, with 64 sites going to muscles of extension, and 64 sites going to muscles of flexion. There are 64 sites on either side of the spine from the shoulders to the top of the pelvis, and 64 sites located bilaterally from the back of the shoulder to just in front of the iliac crest at the waist. Finally, there are 64 sites on either side of the ventral portion of the body extending from the front of the shoulder down past the navel to the top of the thigh.

A nerve impulse or action potential from a motor neuron traveling down the nerve fiber's microtubule arrives at the chemical synapse in a motor endplate region. There it triggers electrochemically, via the neurotransmitter acetylcholine and calcium ions, the continuation of that action potential post-synaptically at a power that is amplified over what came down the nerve fiber originally from the motor neuron. This amplification can be understood easily in terms of the equations of electricity. To amplify the nerve impulse's power in the equation, $P=VI$, the body increases the rate of flow of electrons, I, not V. This rate is increased by the diminution of resistance to the flow of electrons on the post-synaptic transverse tubule of the muscle cell. At a constant V, to increase I, R must be reduced, $V=IR$. With increased I and a constant V, P is increased. Diminution of R may be accomplished by increasing the number of ions moving (since ion movement in an electrolytic cell is R, not I), or by increasing the cross-sectional area of the semiconductor. However, the muscle cell functions well only within certain ranges of ion concentrations. So increasing the cross-sectional area of the conductor, i.e., the transverse tubule, is the way that cell reduces R. The appropriate equation here is $R=1/x^2$ where x is the cross-sectional area of the conductor or semiconductor. If the cross-sectional area of the transverse tubule is twice that of the nerve fiber's microtubule, then the power passed on is amplified four times.

It has long been known that muscle atrophy from disuse results in motor weakness. This is due to the loss of amplification of the power of the nerve message. This amplification of the nerve message is dependent upon the health of the muscle cell. Loss of amplification occurs as the result of the loss of cross-sectional area of the transverse tubule, which is long associated with disuse atrophy of muscle. In order to restore this amplification and with it muscle strength, the transverse tubule's cross-sectional area must be restored.

Traditionally the building of muscle has depended upon its overloading through resistance exercises, weight training. Such overloading is little more than the rapid delivery of impulses causing twitches the sum of which is seen as muscle contraction. Traditional methods of building muscle are nearly useless when the cross-sectional area of the transverse tubule is so diminished that the muscle is extremely weak or not at all usable. Traditional methods of building muscle work well only with healthy muscle and healthy nervous systems. With the ability to simulate the nervous impulse electrochemically comes the ability to trigger the building of muscle unusable from advanced atrophy, the loss of transverse tubule cross-sectional area. Muscle use is not needed to build muscle if electrochemistry is used to overload that muscle. Nor is a healthy or even functioning nervous system necessary as long as nervous system trophism's simulation is provided to a still existing motor endplate region or ganglion. When these endplate regions or ganglia no longer exist, because of severing of the nerve to muscle, the muscle can be seen to display what is called the 'reaction of denervation' on the electromyographer's oscilloscope. If this is found, no amount of electrochemical stimulation will restore the muscle. The muscle's transverse tubule can be energized to grow in cross-sectional area by the delivery of impulses to the site of the motor endplate region at a strength of I and rate of delivery that exceeds that which even a healthy body can provide. In this way the muscle is overloaded just as if it were being subjected to weight training.

Operating in accordance with the present invention results in a sufficient overload to any and all muscles of the body at treatments times preferably of about 1 second to about 2 seconds per day for each and every motor endplate region or ganglion. Such overloading, just as with natural, resistance exercise weight training, triggers the increase of cross-sectional area of the muscle cell's transverse tubule in response. The muscle's contraction is strengthened because of the increased amplification of the power of the nerve impulse across the chemical synapse.

Since what is involved is electrochemistry, every bit of anabolic, muscle building must be balanced by a catabolic, corrosive chemical reaction. Preferably, the pulses are delivered by battery 106 delivering in the range of about 85–90 volts with the building of muscle tissue balanced by the corrosion at cathode 136.

Because electrons, as beta radiation, are an ionizing radiation, treatment times must be limited to prevent damage to the skin. This damage will at first show up to be the same at either pole, a reddening of the skin that will rapidly disappear if noticed early and the electrodes moved regularly. At the current amplitude needed for facial muscle contraction about 10 milliamperes, and a pulse rate of 2000 Hz., treatment times should not exceed eight seconds per motor endplate site. Preferably treatment times should never need to exceed one or two seconds every other day or three times a week to build muscle. At greater current strengths of 10 to 20 milliamperes needed to penetrate to the motor endplate regions of larger muscles like those of the buttocks, back, abdomen or thighs, treatment times should not exceed 5 seconds, and still need not exceed one or two seconds. It may take a few seconds to precisely locate these sites precisely, but when located they need to be stimulated no more than one or two seconds. When the pulse rate is diminished to 1500 Hz. or less, treatment times may be correspondingly lengthened.

When the electrochemical impulse is provided by a condenser that is charged by the rectification of current from a wall socket, for example, the anabolic building of muscle is not balanced by catabolic corrosion in the condenser. The catabolic, corrosive chemical reaction must occur in another form. To prevent the occurrence of this corrosion in the body at the site 60 of cathode 136, the dispersive electrode that withdraws the same number of electrons as delivered to the body by the stimulating electrode, should be made of an easily corroding metal, like iron. In electrochemistry, such a cathode is called a 'sacrificial metal' because its oxidation or rusting provides the electrons delivered by the stimulating electrode used to trigger muscle anabolism, which otherwise must be pulled from the user's body. The net effect of the use of a corroding cathode is the introduction of and supplementation of chemical energy to the body. Without a corroding cathode, what takes place is the existing chemical energy in the body is shifted from one place to another, and not supplemented. This is harsher on the skin beneath the cathode, and tends to cause increased levels of skin ionization at this pole. This ionization is reduced by having the electrons pulled from the metal rather than the body.

The dispersive electrode 136 is designed to have a far greater surface area than that of anodic probe 138. Therefore, electrode 136 may be left in place while the stimulating electrode 138 is selectively positioned to stimulate at site 160 of up to 64 motor endplate regions or ganglia. Dispersive electrode 136 should be at least about 9 square inches in size, whereas the head of stimulating electrode 138 may be as small as about the equivalent of three-quarters of an inch in diameter and preferably is about one inch square. Both electrodes are preferably covered with a cloth absorbent to water, e.g. cotton or similar fabric, as an interface between the electrodes and the skin. By dispersing the charge left by the cathode in the body over a larger area, the intensity of the ionizing effect is diminished per unit area. When the electrodes are allowed to remain in one place for excessive amounts of time, this excess will show up as very dark reddening at either pole that takes longer than 20 minutes to dissipate. The introduction of electrons or beta radiation by anodic, stimulating electrode 138 may cause blistering in this redness area. Excessive skin ionization at the site of cathodic, dispersive electrode 136, on the other hand, will be followed by flaking of the skin within a few days, and, in extreme cases, pitting of the skin rather than blistering. Limiting treatment times and frequent shifting of dispersive electrode 136 is the best way to avoid this ionization. Any damage that the use of electrochemistry might trigger in the body will first appear on the skin where the current strength is strongest. If damage to the skin is avoided, no internal damage will result either.

By stimulating at the motor endplate region or ganglia for 1 to 2 seconds every second or third day, just as with weight training, one may build muscle by overloading it without having to use that muscle. Such building of muscle tissue has never been accomplished by traditional modes of electrotherapy because such modes do not involve electrochemistry and do not take into consideration the importance of the motor endplate regions and ganglia as the indispensable site of delivery of the electrical field.

Pulses from anodic probe 138 of varying waveform and width may accomplish the electrochemical stimulation of muscle by the delivery of beta radiation, electrons or chemical energy to key sites. However, the most efficient and time saving method is the use of a square wave of a pulse width of 0.25 milliseconds duration. I, rate of current flow in V=IR, involves a time factor. At pulse widths less than 0.25 milliseconds, the amount of current passed is so limited as to make any resulting muscle twitch very weak. Toothed waveforms, ramped wave forms, and pulse widths greater than 0.25 milliseconds may also be used, and may trigger the desired twitches. However with longer pulse widths, the preferred frequencies of 2000 Hz. cannot be achieved. This extends treatment times by as much as 2 or 3 seconds per site depending upon the diminished frequency. Since all that is needed is to trigger a twitch, and since this can be done in a little as about 0.25 milliseconds, increased pulse widths tend to be harsher on the skin. Once the muscle twitches, the muscle then relaxes and the current's effects are local to the skin only, even if the current switch is left in the on position. Ionization of the skin is therefore more pronounced when pulse widths exceed 0.25 milliseconds even if the building of muscle is still triggered.

Without departing from the spirit and scope of this invention, one of ordinary skill in the art can make various changes and modifications to the method of the present invention to adapt it to various usages and conditions. As such, these changes and modifications are properly, equitably, and intended to be, within the full range of equivalents of the following claims.

What is claimed is:

1. A method of building muscle through the use of electrochemistry, comprising selectively touching the skin overlying the motor endplate regions/neuromuscular junctions of the muscle with an anodic probe connected to a source of direct current power, for a treatment time in the range of about 1 second to about 8 seconds per treatment, and generating pulses at a current amplitude of from 5 to 25 milliamperes, a voltage in the range of about 50 to about 120 volts, a pulse duration in the range of about 0.2 to about 1 millisecond and at a frequency of at least 1000 Hertz.

2. The method of claim 1, wherein the current amplitude is in the range of about 10 to about 20 milliamperes for treatment times not to exceed 5 seconds every other day.

3. The method of claim 1, wherein the voltage is in the range of about 80 to about 90 volts.

4. The method of claim 1, wherein the anodic probe generates in the range of about 2000 to about 2500 pulses at least two times per week.

5. The method of claim 1, wherein an absorbent cloth separates the skin from the anodic probe.

6. The method of claim 1, wherein a transcutaneous cathode is placed anywhere on the user's body.

7. The method of claim 6, wherein the cathode consists of a corrosive metal.

8. The method of claim 7, wherein the cathode consists of iron.

9. The method of claim 8, wherein the anodic probe contacts an area of the skin equivalent to at least about three-quarters of an inch in diameter and the cathode contacts at least about nine 9 square inches of the body of the user during the selectively touching of the skin.

10. The method of claim 9, wherein an absorbent cloth separates the skin from the cathode.

11. A method of building muscle through the use of electrochemistry, comprising the steps of:

placing a transcutaneous cathode anywhere on the user's body that covers an area of at least 9 square inches of body of the user and consisting of a corrosive metal;

selectively touching an area equivalent to at least about three-quarters of an inch in diameter of the skin overlying the motor endplate region with an anodic probe connected to a source of direct current power, for treatment times in the range of about 1 second to about 8 seconds per site at least two times a week, and generating pulses at a current amplitude of from 5 to 25 milliamperes, a voltage in the range of about 50 to about 120 volts, a pulse duration in the range of about 0.2 to about 1 millisecond and at a frequency of at least 1000 Hertz.

12. The method of claim 11, wherein anodic probe generates in the range of about 2000 to about 2500 pulses at least two times per week.

13. The method of claim 11, wherein an absorbent cloth separates the skin from the anodic probe and the cathode.

14. The method of claim 11, wherein the cathode consists of iron.

* * * * *